United States Patent [19]

Comerford et al.

[11] 4,023,571

[45] May 17, 1977

[54] NON-PLANAR ARCUATE SHAPED ABSORBENT LINER

[75] Inventors: John M. Comerford, Morganville; Mohamed W. Hammad, Old Bridge, both of N.J.

[73] Assignee: Personal Products Company, Milltown, N.J.

[22] Filed: Apr. 21, 1976

[21] Appl. No.: 678,797

[52] U.S. Cl. .................. 128/290 P; 128/290 R; 128/290 B; 128/296; 128/284; 128/288
[51] Int. Cl.² ................................. A61F 13/16
[58] Field of Search .......... 128/284, 287, 286, 288, 128/289, 290 R, 290 W, 290 B, 290 P, 296 288

[56] References Cited

UNITED STATES PATENTS

| | | | |
|---|---|---|---|
| 2,964,040 | 12/1960 | Ashton et al. | 128/290 R |
| 3,095,878 | 7/1963 | Bassett | 128/290 W |
| 3,262,451 | 7/1966 | Morse | 128/290 R |
| 3,316,906 | 5/1967 | Baron | 128/290 W |

*Primary Examiner*—Aldrich F. Medbery
*Attorney, Agent, or Firm*—Jason Lipow

[57] ABSTRACT

An absorbent nether garment liner is provided which comprises an absorbent layer having a first and second major surface and exhibiting an elongation under tensile stress which is recoverable and such stress is relaxed. A body fluid impervious layer overlies and is adhered to the first major surface of the absorbent layer, said body fluid impervious layer exhibiting less recoverable elongation than the absorbent layer. The absorbent layer is adhered to the impervious layer while the former is under tension and hence, elongated. Accordingly, the absorbent nether garment liner will assume a non-planar arcuate shape.

10 Claims, 6 Drawing Figures

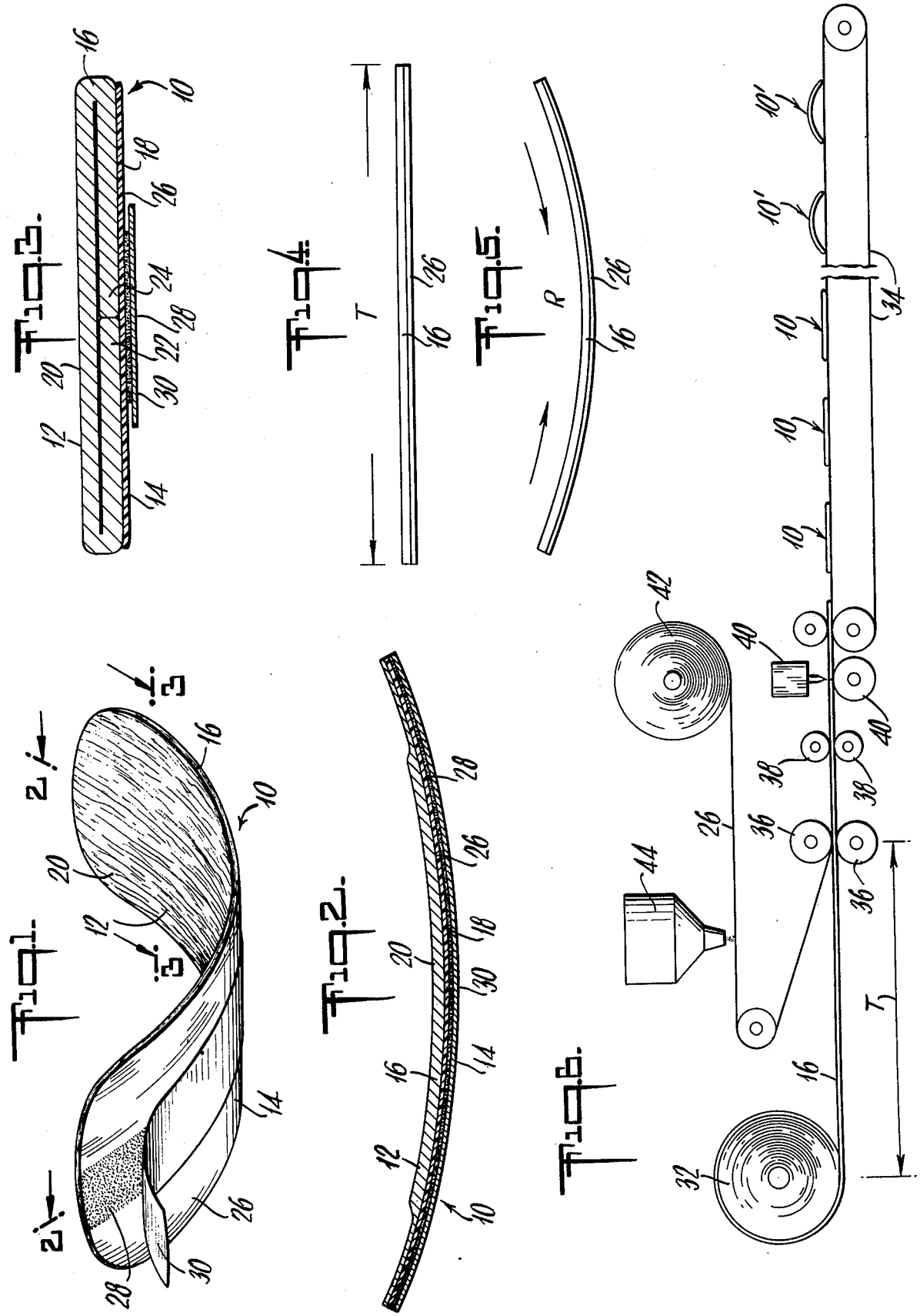

NON-PLANAR ARCUATE SHAPED ABSORBENT LINER

BACKGROUND OF THE INVENTION

This invention relates to absorbent liners for nether garments such as, for example, sanitary napkins, panty shields and the like. The function of such products is to be placed against the body and, specifically, between the body and the nether garment whereby the product may absorb and retain fluid exuded from the body and hence protect the nether garment from soiling or staining.

Such products now on the market are generally made in a flat or planar form. However, in order to function properly, the product should be held in intimate contact with the body. Since, in most cases, the configurations of the particular parts of the body against which the products are to be placed in use are not flat, it is necessary to distort these originally flat products into nonplanar configurations. For example, panty shields now on the market are flat and planar, yet are designed to fit, by adhesive attachment, to the crotch portion of an undergarment and to closely conform to the vaginal area of the wearer. Clearly, the flat product must be distorted to conform to the generally arcuate shape of the body, i.e., the product must assume a non-planar, arcuate shape being concave inward with respect to the body contacting surface.

The necessary distorting of such originally flat products has resulted in unsatisfactory performance. In particular, when so distorting these products which are generally made up of one or more layers of fibrous absorbent material, creases and folds result causing great discomfort to the wearer. Additionally, such creases and folds cause portions of the product to stand away from close contact with the body and hence, the primary absorbing function of the product is greatly impaired.

Suggestions already exist for manufacturing arcuate absorbent products, yet to date, no such product has met with any commercial success. This failure of prior art suggestions is generally due to the fact that the kinds of absorbent products considered herein are of the disposable variety and must be manufactured at great speed and for an extremely low unit cost in order to be commercially viable. The very nature of a non-planar product has heretofore been incompatible with high speed, straight line, continuous manufacturing processes. Additionally, the methods devised by prior art suggestions require costly processing steps and raw materials and hence, have been unacceptable.

A specific example of such prior art suggestion is that disclosed in U.S. Pat. No. 3,262,451 issued to Edward A. Morse on July 26, 1966. Described therein is an arcuate absorbent pad which is first manufactured in a planar shape but upon subsequent treatment, takes on the desired non-planar arcuate shape. This change in shape is accomplished by adhering to the absorbent pad or embedding within the absorbent pad a layer of so-called "heat-shrinkable" polymeric film. Such film has the property of shrinking when subjected to a heating. According to the method of Morse, the flat product comprising the absorbent pad and film is subjected to a heating step which shrinks the film and induces the product to assume an arcuate shape. Unfortunately, this product and method has not had commercial success primarily because of the above mentioned factors, to wit: the heating step introduces complexities and expense into the high speed manufacture of such a product and the special film is relatively expensive when compared to materials normally employed in such products. Accordingly, there is still an unfulfilled need for a simple, economically manufactured, non-planar, arcuate absorbent nether garment liner.

SUMMARY OF THE INVENTION

It has now been discovered that a non-planar, arcuate shaped absorbent nether garment liner may be provided without the drawbacks associated with prior suggestions. In particular, such a liner may be manufactured from relatively inexpensive and readily available materials using a process which introduces no complexities or added expense to the product.

Specifically, an absorbent nether garment liner is provided comprising an absorbent layer having a first and second major surface. The absorbent layer is chosen to be of a material exhibiting an elongation under a tensile stress that is recoverable when the stress is relaxed. Said in other words, the absorbent layer must exhibit the property of elasticity and must be able to deform under a stress and then recover at least partially from such deformation when the stress is relaxed. Such a material is hereinafter referred to as having "elastic recovery" or being "elastic" or having "elasticity". Overlying and adhered to the first major surface of the absorbent layer is a body fluid impervious layer which exhibits less recoverable elongation, i.e., less elastic recovery, when subjected to the same stress as the absorbent layer. Preferably, the inpervious layer is essentially inelastic under the tension applied in the manufacturing process. The nether garment liner of this invention is further characterized by being essentially planar and flat under tension and assuming a non-planar arcuate shape which is concave inward toward the second major surface of the absorbent layer when such tension is relaxed.

The above described product may be manufactured by adhering the relatively inelastic impervious layer to the elastic absorbent layer while the latter is in an elongated state, i.e., while the absorbent layer is under tension.

The resulting laminate will automatically assume the above described non-planar shape upon release of such tension owing to the difference in the elasticities between the two layers. Thus, for example, in the manufacturing line, long strips of the elastic absorbent material may be provided in rolled form and may be unwound and pulled through rollers creating a tension in the material. The inelastic body fluid impervious layer may be similarly provided in long strips and in rolled form. Adhesive may be applied to one of the two layers and the two may then be joined in face to face relationship, still maintaining tension in the absorbent material. The resulting laminate may then pass a cutting station where it is cut into individual liners while the cutting simultaneously relieves the tension in the cut liner. As the elastic absorbent layer recovers, the cut individual liners assume the arcuate non-planar shape described herein.

In a preferred embodiment, the elastic absorbent is chosen to have the additional property of delayed recovery. That is to say, upon the release of tension, the recovery of elongation, while beginning essentially immediately, proceeds relatively slowly and hence, the liner does not appear to take a non-planar form until some substantial period of time has passed. This is advantageous when considered in connection with the manufacturing process described above. When, in such a process, the laminate is cut into individual liners, the liners will remain flat and planar for a period of time. Accordingly, they may be easily handled and packaged in the flat condition and will only assume their ultimate non-planar shape after being inserted into the packaging container. It is necessary, of course, to package these liners in a container having sufficient room to allow the liners to assume the non-planar shape.

BRIEF DESCRIPTION OF THE DRAWINGS

Referring to the drawings:

FIG. 1 is a perspective view of an absorbent nether garment liner embodying the teachings of this invention;

FIG. 2 is a longitudinal cross-sectional view of the garment liner of FIG. 1 taken along line 2—2;

FIG. 3 is a transverse cross-sectional view of the garment liner of FIG. 1 taken along line 3—3;

FIG. 4 is a schematic longitudinal cross-sectional view of the nether garment liner of this invention under tension;

FIG. 5 is a schematic longitudinal cross-sectional view of the nether garment liner of this invention as it assumes a relaxed state; and FIG. 6 is a schematic longitudinal cross-sectional view of a portion of a machine line for producing the garment liner of this invention.

DETAILED DESCRIPTION OF THE INVENTION

FIGS. 1–3 illustrate an exemplary embodiment 10 of the garment liner of this invention which is shown with the major surface 12, intended to contact the body, facing generally upward in the drawings and with the major surface 14, intended to contact the garment, facing generally downward. As can be seen, the liner has a non-planar arcuate shape which may be characterized as being concave toward the upward facing body contacting surface 12.

The liner 10 is comprised of an absorbent layer 16 having major surfaces wherein in the embodiment shown in FIG. 1, the first major surface 18 is on the garment contacting side of the liner and the second major surface 20 is on the body contacting side and coincides with surface 12.

The absorbent layer 16 is chosen from material having the ability to absorb body fluids and is soft and comfortable when placed against the body. Additionally, the absorbent layer as a whole must have sufficient structural integrity to allow for handling during manufacture and in use. In accordance with the teachings of this invention, the absorbent layer is chosen from material which also exhibits the property of elastic recovery, i.e., which can be elongated under a tensile stress (imposed in the longitudinal direction of the liner 10 illustrated in the drawings) and will recover at least partially from such deformation when the stress is relaxed. It is preferred that the selected absorbent layer have a percent elongation to break (i.e., an increase in length just prior to failing under a tensile stress) of at least about 1% based on the original unstressed length and preferably at least about 5%. The elastic recovery from such elongation may be relatively small, provided, as will be explained in greater detail herein, it is greater than that of the impervious layer to which the absorbent layer is to be adhered. It is sufficient then that the percent recovery of the absorbent layer, when relaxing from a given stress, be at least 10% greater than that of the impervious layer relaxing from the same stress. Preferably, however, the absorbent layer should be capable of recovering at least 20% more than the impervious layer. Said in other words, the ratio of the percent recovery of the impervious layer to that of the absorbent layer is no greater than 0.9% and preferably no greater than 0.8%.

A wide variety of absorbent material is suitable for use in the liners of this invention. For example, the absorbent layer may comprise one or more layers of absorbent creped tissue having the requisite elastic properties. Alternatively, the absorbent layer may comprise other woven or nonwoven webs of absorbent fibers which are not in themselves elastic but are admixed with elastic fibers, at least some of which are in the machine direction and which give the web the requisite elasticity. Still another possibility is to provide an elastic scrim interposed between two relatively inelastic webs so that the composite laminate will have the requisite elasticity. Common particulate absorbent materials such as comminuted wood pulp fibers, cotton linters, rayon fibers, cotton staple and the like may be utilized provided they can be formed into a layer which has structural integrity and which has the requisite elastic properties. One method of providing such a layer with structural integrity is to bond the particulate absorbent matter together using any of the common binders now on the market. Elasticity may be obtained by using an elastic binder such as, for example, styrene butylene or the like. Structural integrity may also be obtained by enclosing the particulate matter in a woven or nonwoven wrapper to form a wrapped pad. In this case, the wrapped particulate matter as a whole will constitute the absorbent layer of this invention and may be given elastic properties by choosing an elastic wrapping material or by incorporating an elastic scrim into the wrapped pad. Still another possibility is to form the absorbent layer of a synthetic elastic absorbent material such as the newly developed hydrophilic polyurethane foams. Undoubtedly, many other variations and combinations of the above described materials will occur to one skilled in the art for employment in accordance with the teachings of this invention.

In the liner of FIGS. 1–3, a particularly suitable absorbent layer material is employed by way of example. This material is the lofty and soft nonwoven through bonded fabric described in U.S. Pat. No. 3,663,238, issued on May 16, 1972 to G. J. Liloia et al. This fabric consists essentially of a mixture of approximately 25% by weight of long (about 2.9 cms) rayon fibers and about 75% by weight of short (about 0.2 cm) pulp fibers and has a water dispersible binder applied throughout in an amount between about 1% and about 30% of the weight of the fibers on a dry solids basis. The binders of choice are the self-curing acrylic latex family, the urethane family or other binders which can be ultilized in low viscosity solutions or suspensions and give the fabric the requisite properties. The fabric has a weight of less than about 8 ounces per square yard and a density of about 0.15 to about 0.05 gm. per cc. and may be characterized as being absorbent and extremely soft and lofty. Because of the through bonding, the fabric is capable of maintaining its structural integrity without the need for a wrapper material. The fabric has a percent elongation to break of about 10% and an elastic recovery of about 70% of said elongation. Thus, for example, a 10 inch length of the fabric may be stretched to 11 inches before breaking and when relaxed, will shrink to a length of 10.3 inches.

As is best illustrated in FIG. 3, a double thickness of the fabric is employed by folding the longitudinal, peripheral edges 22, 24 of a sheet of the fabric toward the center to form the absorbent layer 16. These edges may be held in place by the application of adhesive or other means known in the art (not shown in the drawings).

Overlying and adhered to the first major surface 18 of the absorbent layer 16 is a body fluid impervious layer 26 which in addition to the function of cooperating with the absorbent layer 16 to provide the non-planar arcuate shape, also serves to act as a barrier to body fluids and prevent the "strike through" of such fluids onto the nether garment. Generally, the layer must have, in accordance with the teachings of this invention, less elastic recovery than the absorbent layer under the same conditions. Preferably, the impervious layer has essentially no elastic recovery. A wide variety of readily available materials are suitable for use as the impervious layer of this invention. Such layer may comprise, for example, a polymeric film, e.g., polyethylene, polypropylene, cellophane or even a normally fluid pervious material that has been treated to be impervious such as impregnated fluid repellant paper. It will be appreciated by one skilled in the art that materials which normally do not exhibit the inelasticity prescribed by the teachings of this invention may be employed as the impervious layer provided that they have been sized or otherwise treated to become inelastic.

The garment liner illustrated in FIGS. 1-3 is of the type intended to be worn by being adhered to the crotch portion of a panty or other undergarment by means of adhesive attachment. To this end, the garment contacting side of the impervious layer 26 is provided with a longitudinally and centrally located pressure sensitive adhesive element 28 which serves to adhere the liner to the garment. This adhesive element may comprise any of a large number of pressure sensitive adhesives already available on the market including, for example, the water based pressure sensitive adhesives such as the acrylate adhesives, for example, vinyl acetate-2 ethyl hexyl acrylate copolymer which is generally combined with tackifiers such as, for example, ethylene amine. Alternatively, the adhesive may comprise the rapid setting thermoplastic (hot melt) adhesives such as block copolymers exemplified by styrene and butadiene styrene copolymers. The adhesive element may also comprise a two sided adhesive tape.

Overlying the full length of the adhesive element 28 is a protective release strip 30, illustrated in FIG. 1, as being partially peeled away from the adhesive. The strip 30 is provided to protect the adhesive element from dirt and from unintentional adhesion prior to use and may be made of any suitable sheet-like material which adheres with sufficient tenacity to the adhesive element 28 to remain in place, but which can readily be removed when the liner 10 is to be used. A particularly useful material is a semi-bleached kraft paper, the adhesive contacting side of which has been silicone coated to provide for easy removal from the adhesive element 28.

While the invention has been illustrated in FIGS. 1-3 in connection with an adhesively attached liner, it will be apparent that the advantages disclosed herein apply to otherwise attached liners such as those utilizing pins, belts and the like.

As is described above, the liner of this invention has the property of being generally flat and planar when under tensile stress. Owing to the difference in elasticity between the absorbent layer 16 and the fluid impervious layer 26, the liner will assume the desired non-planar arcuate shape in the relaxed state. This property of the liner is best illustrated by the schematic representatives of FIGS. 4 and 5. In these FIGURES, the liner has been reduced to its simplest form, namely, a laminate of the elastic absorbent layer 16 and the relatively inelastic fluid impervious layer 26. In FIG. 4, the absorbent layer 16 is adhered to the impervious layer 26 while the absorbent layer is under a tensile stress (the forces of which are indicated by the letter T and the arrows) and hence, elongated. In this condition, the liner is relatively flat and planar. As is shown in FIG. 5, when the tensile stress is removed, recovery forces arising from the elastic recovery of the absorbent layer 16 (represented by the arrows and the letter R) tend to act to shrink the absorbent layer while at the same time, these forces are resisted by the relatively inelastic layer 26. In order for the absorbent layer to shrink while the impervious layer remains about the same length, the liner is induced into the non-planar arcuate shape illustrated in FIG. 5.

Schematically illustrated in FIG. 6 is a portion of a production line which may be employed to produce the simplified liner illustrated in FIGS. 4 and 5. Shown therein is a supply roll 32 of the absorbent layer 16 which is wound with the material under tension and hence, elongated on the roll. The roll 32 is unwound and carried to an endless belt 34 through the nip of adhering rollers 36 and tension rollers 38 to cutting rollers 40. By means of these rollers, further tension is applied to the layer 16 (as indicated by the letter T and the arrows) and the layer 16 is in a further elongated state. Such tension, for example, may vary from about 10 to 200 gms. per inch of width of said absorbent layer. Preferably, such tension will vary from 25 to 125 gms. per inch of width. A second supply roll 42 of the impervious, in elastic layer 26 is unwound and passed under an adhesive applicator 44 where adhesive is applied thereto. The two layers are joined and adhered together in the nip of the adhering rollers 36 and the joined layers are then carried through the nip of tension rollers 38 to cutting station 40 where the joined laminate is cut into individual liners 10. It should be noted that up until the point where individual liners are severed from the remainder of the joined layers, the absorbent layer 16 is under tension and elongated, and also in a flat, planar shape. Upon being cut, the severed individual liner 10 is no longer under such tension and owing to the elasticity of the absorbent layer, recovery forces such as are described in connection with FIG. 5 begin to induce the liner 10 into a non-planar, arcuate shape, as depicted in FIG. 6 by liner 10'. The elapsed time between the severing of the individual liners 10 and when the liner assumes the shape shown in FIG. 10' should preferably be as long as possible to allow relatively flat products to be positioned in an orderly overlapping manner on a conveyor which carries them to the packaging unit. Accordingly, it is highly desirable that the absorbent layer material be chosen to have, in addition to the other requisite properties, the property of slow recovery. Said in other words, the recovery time in which the material shrinks to its relaxed stable length should be as long as possible. The fabric described above in connection with FIGS. 1-3 is particularly well suited in that this fabric has a very slow recovery time.

We claim:

1. An absorbent nether garment liner comprising:
   an absorbent layer having a first and second major surface, said absorbent layer exhibiting an elongation under tensile stress which is recoverable when said stress is relaxed;
   a body fluid impervious layer overlying and adhered to said first major surface, said body fluid impervious layer exhibiting less recoverable elongation than said absorbent layer;
   said absorbent nether garment liner being essentially planar and flat under tension and assuming a nonplanar arcuate shape, concave inward toward said second maor major when said tension is relaxed.

2. The absorbent nether garment liner of claim 1 wherein said absorbent layer has a percent elongation to break of at least one percent.

3. The absorbent nether garment liner of claim 2 wherein said absorbent layer has a percent elongation to break of at least five percent.

4. The absorbent nether garment liner of claim 1 wherein the ratio of the percent recovery of said impervious layer to that of said absorbent layer is less than 0.9.

5. The absorbent nether garment liner of claim 4 wherein the ratio of the percent recovery of said impervious layer to that of said absorbent layer is less than 0.8.

6. The absorbent nether garment liner of claim 1 wherein said impervious layer is polyethylene film.

7. The absorbent nether garment liner of claim 1 wherein said absorbent layer is a lofty and soft nonwoven, through bonded fabric comprising a machine laid web having a machine direction and a cross direction, said fabric consisting essentially of predominantly short fibers, a minor percentage of long fibers and a low viscosity, water dispersible binder applied throughout said fabric in an amount between about 1 percent and about 30 percent of the weight of the fibers on a dry solids basis, said short fibers comprising cellulosic fibers having lengths less than one quarter inch, said cellulosic fibers comprising no less than about 75 percent by weight of the fiber content of said fabric, said long fibers comprising separated synthetic fibers having substantially uniform lengths greater than three quarters inch, said synthetic fibers comprising no more than about 25 percent by weight of the fiber content of said fabric, said short fibers and said long fibers being substantially randomly disposed and distributed throughout said fabric, said fibers being interconnected by said binder to form a network, said web having a greater tensile strength in the machine direction in comparison to the tensile strength in the cross direction, said fabric having a weight of less than about 8 ounces per square yard and a density of about 0.15 to about 0.05 gram per cubic centimeter.

8. A method of making an absorbent nether garment liner comprising:
   selecting an absorbent layer having a first and second major surface and exhibiting an elongation under tensile stress which is recoverable when said stress is relaxed;
   selecting a body fluid impervious layer exhibiting less recoverable elongation than said absorbent layer;
   adhering said impervious layer to said first major surface of said absorbent layer to form said liner while maintaining said absorbent layer under an elongating tension and essentially flat; and
   relaxing said tension whereby said liner assumes a non-planar arcuate shape being concave inward toward said second major surface.

9. The method of claim 8 wherein said elongating tension is from about 10 to about 200 gms. per inch width of said absorbent layer.

10. The method of claim 9 wherein said elongating tension is from about 25 to about 125 gms. per inch width of said absorbent layer.

* * * * *

UNITED STATES PATENT AND TRADEMARK OFFICE
CERTIFICATE OF CORRECTION

PATENT NO. : 4,023,571
DATED : May 17, 1977
INVENTOR(S) : John M. Comerford et al It is certified that error appears in the above-identified patent and that said Letters Patent are hereby corrected as shown below:

In Column 2, line 32, "inpervious" should read --- impervious ---.

In Column 4, line 49, "U.S.Pat.No.3,663,238" should read --- U.S.Pat.No.3,663,348 ---.

In Column 7, line 18, Claim 1, "maor" should be deleted.

In Column 7, line 18, Claim 1, after "major" insert --- surface ---.

Signed and Sealed this

Twenty-fifth Day of July 1978

[SEAL]

Attest:

RUTH C. MASON
Attesting Officer

DONALD W. BANNER
Commissioner of Patents and Trademark